US00PP24168P2

(12) United States Plant Patent
Kolster

(10) Patent No.: US PP24,168 P2
(45) Date of Patent: Jan. 21, 2014

(54) *STYRAX* PLANT NAMED 'EVENING LIGHT'

(50) Latin Name: *Styrax japonicus*
Varietal Denomination: EVENING LIGHT

(76) Inventor: Henny Kolster, Boskoop (NL)

( * ) Notice: Subject to any disclaimer, the term of this patent is extended or adjusted under 35 U.S.C. 154(b) by 39 days.

(21) Appl. No.: 13/506,694

(22) Filed: May 11, 2012

Related U.S. Application Data

(60) Provisional application No. 60/519,756, filed on May 31, 2011.

(51) Int. Cl.
*A01H 5/00* (2006.01)

(52) U.S. Cl.
USPC ..... Plt./216

(58) Field of Classification Search
USPC ..... Plt./216, 226
See application file for complete search history.

*Primary Examiner* — Kent L Bell

(57) ABSTRACT

A new cultivar of *Styrax* plant named 'EVENING LIGHT' which exhibits an upright vase-shaped habit with foliage that emerges and remains rich dark purple to black when grown in full sun. When grown in shade, the older lower leaves of 'EVENING LIGHT' become dark olive green or bronze in color. 'EVENING LIGHT' bears pure white to very pale pink bell-shaped flowers in May and June. 'EVENING LIGHT' prefers sandy soil and is hardy to USDA Zone 5. In combination these traits set 'EVENING LIGHT' apart from all other existing varieties of *Styrax* known to the inventor.

3 Drawing Sheets

Genus: *Styrax*.
Species: *japonicus*.
Denomination: 'EVENING LIGHT'.

BACKGROUND OF THE INVENTION

The present invention relates to a new and distinct cultivar of *Styrax*, commonly known as Japanese Snowbell that is grown for use as a small tree. It is known botanically as *Styrax japonicus* and will be referred to hereinafter by the cultivar name 'EVENING LIGHT'.

'EVENING LIGHT' was discovered by the inventor in 2001 at the inventor's nursery in Boskoop, the Netherlands as a chance seedling which arose in the nursery amongst other seedlings of unnamed *Styrax* raised by the inventor. The inventor observed that one seedling, initially named "Kolster Purple" and later named 'Evening Light' exhibited dark purple foliage when grown in full sun. The inventor observed this one seedling into maturity and commenced propagation when the plant was five years of age.

The variety of *Styrax* which is considered by the inventor to most closely resemble 'EVENING LIGHT' is *Styrax* 'Purple Dress' (unpatented). The foliage of 'EVENING LIGHT' is more elongated when compared with the broad leaves of 'Purple Dress'. Whereas the foliage of 'Evening Light' emerges and remains glossy dark purple to black when grown in full sun, the foliage of 'Purple Dress' emerges reddish-brown and becomes matte olive-green by summer.

Asexual reproduction of 'EVENING LIGHT' was first accomplished by the inventor in 2006 in a cultivated area of Boskoop, the Netherlands. Asexual propagation was accomplished by grafting 'EVENING LIGHT' onto *Styrax* seedling understock. Since that time the distinguishing characteristics of 'EVENING LIGHT' have been determined stable and uniform and to reproduce true to type in successive generations of asexual propagation by other means including semi-hardwood cuttings.

SUMMARY OF THE INVENTION

The following traits have been repeatedly observed and represent the characteristics of the new *Styrax* cultivar 'EVENING LIGHT'. These traits in combination distinguish 'EVENING LIGHT' from all other varieties of *Styrax* known to the inventor. 'EVENING LIGHT' has not been tested under all possible conditions and phenotypic differences may be observed with variations in environmental, climatic and cultural conditions, without however any change in genotype.

1. Plants of 'EVENING LIGHT' exhibits an upright vase-shaped habit.
2. The foliage of 'EVENING LIGHT' emerges and remains rich dark purple to black when grown in full sun.
3. When grown in shade, the older lower leaves of 'EVENING LIGHT' become dark olive green or bronze in color.
4. 'EVENING LIGHT' bears pure white to very pale pink bell-shaped flowers in May and June and which are formed on young wood.
5. At four years of age, plants of 'EVENING LIGHT' are 1.5 m in height and 0.7 m in spread.
6. At ten years of age, plants of 'EVENING LIGHT' are 3 m in height and 1.2 m-1.5 m in spread.
7. 'EVENING LIGHT' prefers sandy soil.
8. 'EVENING LIGHT' is hardy to USDA Zone 5.

BRIEF DESCRIPTION OF THE DRAWINGS

The accompanying color drawings illustrate the overall appearance of the new *Styrax* variety 'EVENING LIGHT' showing colors as true as it is reasonably possible to obtain in colored reproductions of this type. Colors in the drawings may differ from the color values cited in the detailed botanical description, which accurately describe the actual colors of the new variety 'EVENING LIGHT'.

The drawing labeled

The drawing labeled

Figure 1:
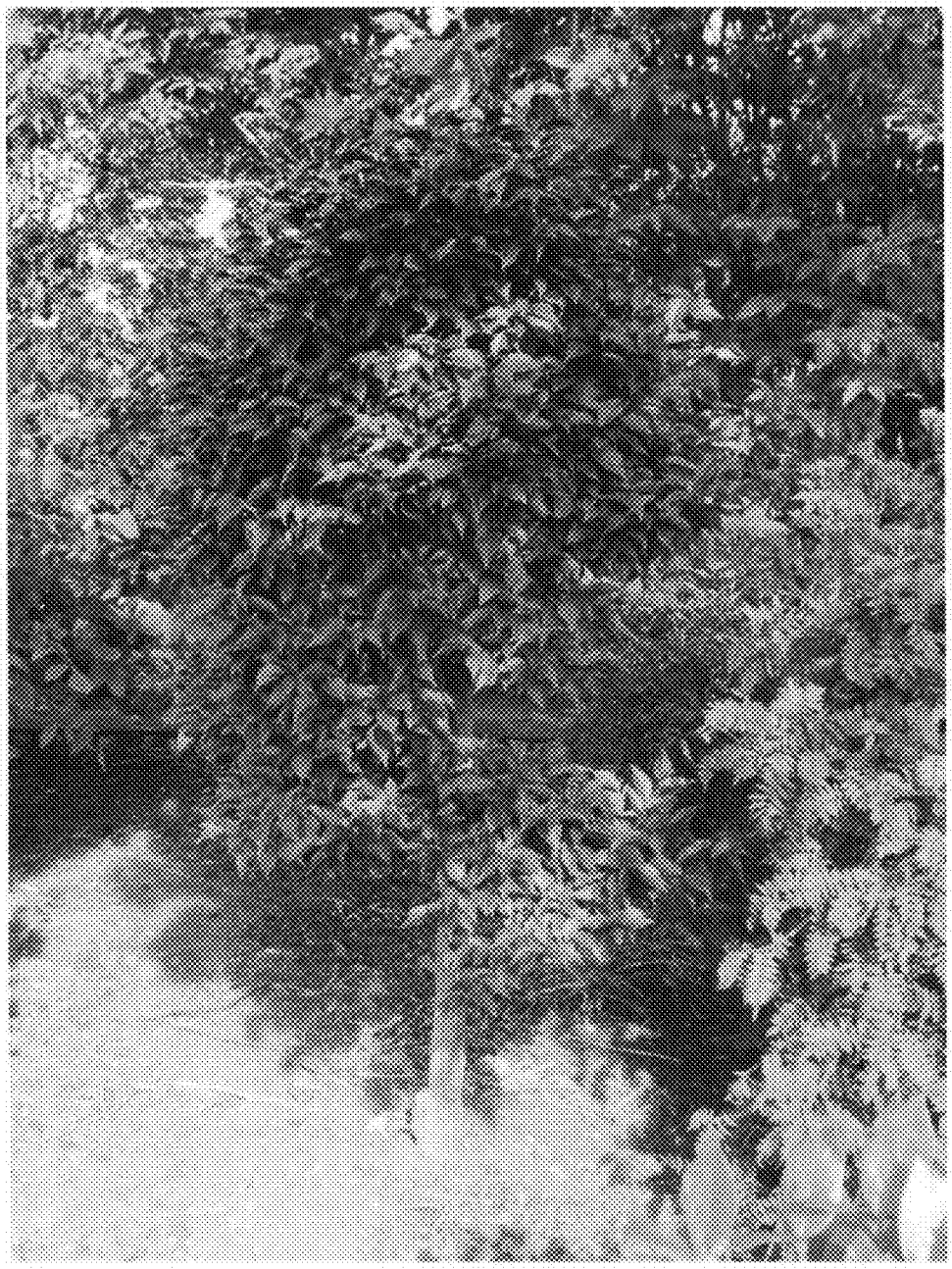
FIG. 1 shows the inventor's original selection as a 10 year old tree which has been grown out of doors by the Breeder in his landscape in Boskoop, The Netherlands. This drawing illustrates the dark foliage of 'EVENING LIGHT' wherever it is exposed to full sun and not shaded by adjacent plant material or its own leaf canopy.
Figure 2:
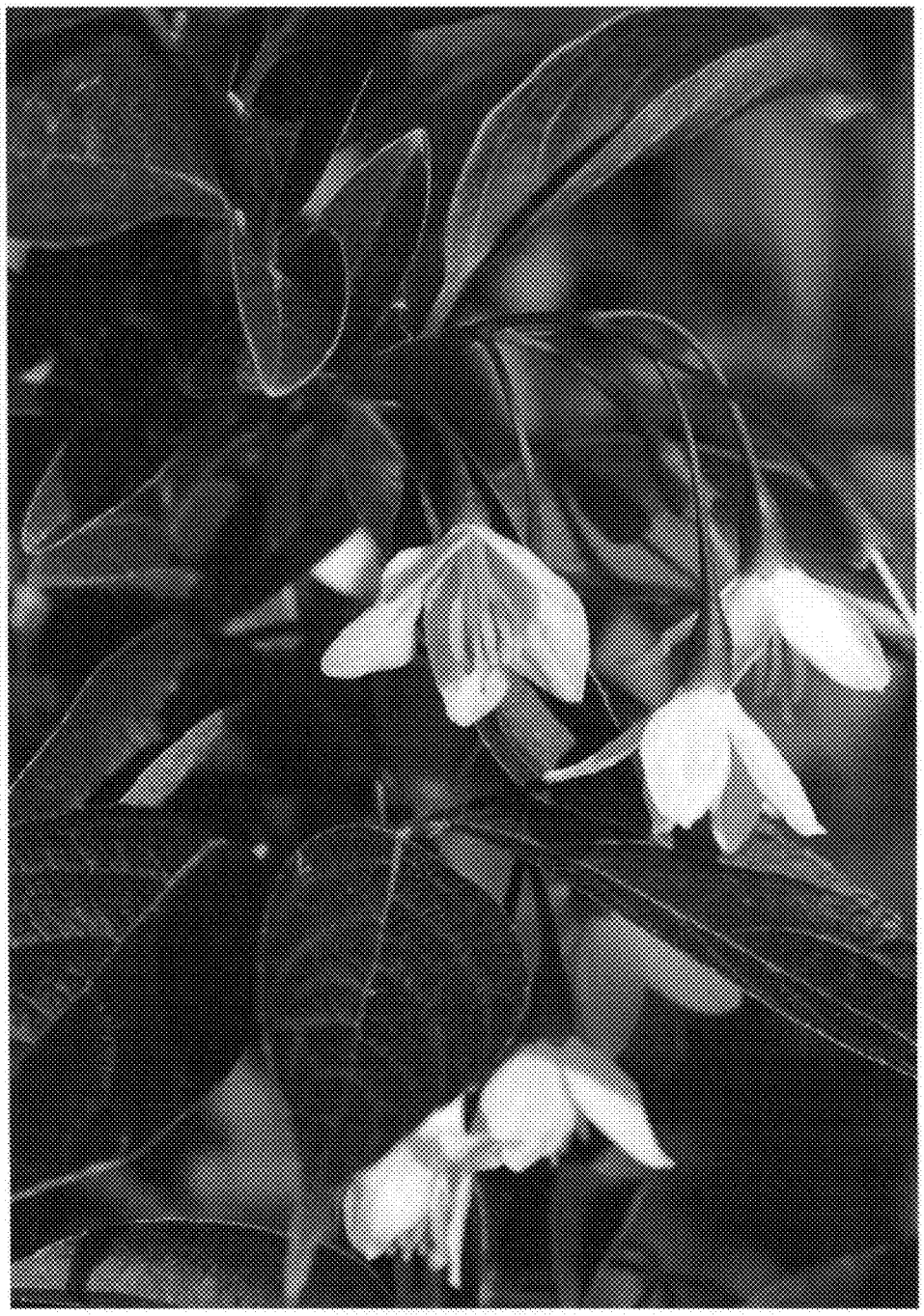
FIG. 2 illustrates the white to very pale pink bell-shaped flowers of 'EVENING LIGHT'.
Figure 3:
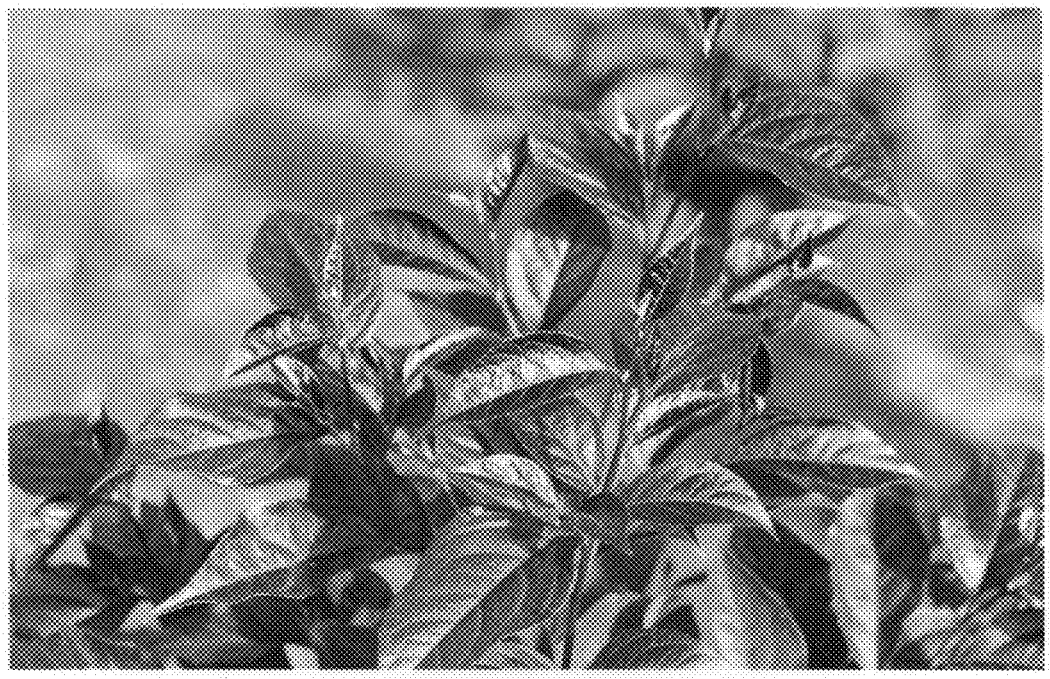

The drawing labeled as FIG. 3 illustrates the uppermost foliage of a four year old tree of 'EVENING LIGHT'. Under these conditions of full sun exposure the juvenile and mature foliage is glossy dark purple to black.

All drawings were made using conventional techniques and although colors may appear different from actual colors due to light reflectance they are as accurate as possible by conventional photography.

BOTANICAL DESCRIPTION OF THE PLANT

The following is a detailed description of the new cultivar 'EVENING LIGHT'. Data was collected from 4 years-old plants grown out of doors in Mollala, Oreg. The color determinations are in accordance with the 2007 edition of The Royal Horticultural Society Colour Chart of The Royal Horticultural Society, London, England, except where general color terms of ordinary dictionary significance are used. No chemicals were used to treat the plants. Growing conditions are typical to other *Styrax*.

Botanical classification: *Styrax*.
Species: *japonicus*.
Common name: Japanese Snowbell.
Commercial classification: Deciduous flowering tree.
Use: Landscape plant.
Parentage: *Styrax japonicus* (chance seedling).
Plant description:
- *Plant habit*.—Upright, vase-shaped.
- *Plant dimensions* (4 *years*).—1.5 m in height, 0.7 m in spread.
- *Plant dimensions* (10 *years old*).—3 m in height 1.2 m, 1.5 m in spread.
- *Plant hardiness*.—USDA Zone 5.
- *Type*.—Deciduous flowering tree.
- *Propagation*.—Grafting, budding, or with semi-hardwood cuttings.
- *Growth rate*.—Vigorous.
- *Cultural requirements*.—Moist light sandy soil with good drainage.
- *Diseases and pests*.—None known to the inventor.

Stem:
- *Shape*.—Cylindrical.
- *Dimensions*.—4 year old plant, trunk: Length 1 m; diameter (at 10 cm above ground level): 2.5 cm-3.0 cm. 4 year old plant, current year's growth: Length 50 cm-75 cm; diameter 3 mm-5 mm.
- *Internode length*.—An average of 2.5 cm.
- *Color*.—Trunk, below leaf canopy: 162D. Stems and lateral stems: Ranges between 172B and 46A.
- *Surface*.—Trunk: Smooth bark except for longitudinal fissures, lenticels absent. Current year juvenile growth lightly pubescent, otherwise smooth.

Foliage:
- *Leaves*.—Arrangement: Alternate. Division: Simple. Shape: Elliptic to elliptic-lanceolate. Dimensions: Approximately 4-7.2 cm in length and 1.5-3.5 cm in width. Apex: Acuminate. Base: Acute. Venation pattern: Reticulate.
- *Leaf and vein color*.—The foliage of 'EVENING LIGHT' emerges and remains rich dark purple to black when grown in full sun (hereinafter "dark leaves"). When grown in shade, the older lower leaves of 'EVENING LIGHT' become dark olive green or bronze in color (hereinafter "green leaves"). Dark leaves: Vein color (adaxial): 200A. Vein color (abaxial): 200C. Margin type: Serrate. Surface texture: Upper surface glossy; lower surface matte. Leaf color (both young and mature leaves, adaxial surface): N186A and darker, almost to black 202A. Leaf color (both young and mature leaves, abaxial surface): 200A. Attachment: Petiolate. Petiole: Dimensions: 11 mm in length and 1.5 mm in diameter. Surface: Smooth with light pubescence when foliage emerges. Color: N199A.
- *Green leaves*.—Vein color (both surfaces): 148B. Margin type: Serrate. Surface texture: Upper surface glossy; lower surface matte. Young leaf color (both surfaces): 137A. Mature leaf color (adaxial surface): Ranges between 137A and N137A. Mature leaf color (abaxial surface): Ranges between 146A and 152A. Attachment: Petiolate. Petiole: Dimensions: 11 mm in length and 1.5 mm in diameter. Surface: Smooth with light pubescence when foliage emerges. Color: 152C.

Inflorescence:
- *Form*.—Pendulous raceme.
- *Arrangement*.—Terminal.
- *Quantity of flowers per inflorescence*.—4 to 8.
- *Flowering period*.—May and June: plant is in bud and flower for approximately five weeks.
- *Lastingness of individual flower after first opening*.—Approximately 2 weeks in mid May and 1 week in mid June.
- *Flower*.—Diameter of flower (including calyx, corolla, petals): 2.5 cm. Height of flower: 1.5 cm. Bud shape: Oval. Bud color: White, closest to N155B. Bud surface: Smooth. Bud dimensions: 11 mm in length and 6 mm in diameter. Calyx: Campanulate. Sepals: 5, fused except for apex. Sepal Apex: Obtuse. Sepal Color: As peduncle 180A, or lighter 180B. Sepal surface: Glabrous. Corolla dimensions: Approximately 1.2 cm in length and 2.5 cm in width. Corolla surface: Glabrous. Corolla tube color: Whitish, ranging between N155C and 157C. Number of petals: 5. Petals fused or unfused: Unfused. Petal shape: Ovate. Petal color (both surfaces): White to very pale pink, ranges from NN155D to N155B. Petal surfaces (both): Smooth. Peduncle shape: Cylindrical. Peduncle dimensions: 1.5 cm to 3.5 cm in length and 0.5 mm to 1.5 mm in diameter. Peduncle color: 180A. Peduncle surface: Glabrous.

Reproductive organs:
- *Pistil*.—1 in number.
- *Pistil dimensions*.—1.5 cm in length.
- *Pistil color*.—N155B.
- *Pistil surface*.—Smooth.
- *Stigma shape*.—Rounded.
- *Stigma dimensions*.—Approximately 0.5 mm in length and 0.5 mm in width.
- *Stigma color*.—N155B.
- *Style shape*.—Linear.
- *Style dimensions*.—Approximately 16 mm in length and 1 mm in width.
- *Style color*.—N155B.
- *Number of stamens*.—10.
- *Stamens fused or unfused at base*.—Unfused.

*Stamen dimensions.*—10 mm in length and 0.8 mm in width.
*Stamen color.*—N155B.
*Anther shape.*—Linear.
*Anther dimensions.*—6 mm in length and 1.0 mm-1.2 mm in width.
*Anther color.*—24C.
*Pollen color.*—13A.
*Pollen amount.*—Slight.
*Ovary position.*—Superior.
*Ovary shape.*—Rounded.
*Ovary dimensions.*—4 mm in length and 3 mm in width.
*Ovary color.*—N186C.

Fruit and seed:
*Fruit.*—Dry drupe, ovoid, 1 cm in length, 0.8 cm in diameter.
*Fruit color.*—Pale gray-green, 193C.
*Quantity of seeds per capsule.*—Typically 1, occasionally 2 or 3.
*Seed shape.*—Ovoid with acute apex and base.
*Dimensions of seed.*—8 mm in length, 5 mm in diameter.
*Color.*—Ranges between 166B and 166C.

The invention claimed is:

1. A new and distinct cultivar of *Styrax* plant named 'EVENING LIGHT' as described and illustrated herein.

* * * * *